United States Patent
Tice

(10) Patent No.: US 9,060,681 B2
(45) Date of Patent: Jun. 23, 2015

(54) TREND MONITORING SYSTEM WITH MULTIPLE ACCESS LEVELS

(75) Inventor: Lee D. Tice, Bartlett, IL (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 1573 days.

(21) Appl. No.: 11/172,106

(22) Filed: Jun. 30, 2005

(65) Prior Publication Data

US 2007/0004970 A1 Jan. 4, 2007

(51) Int. Cl.
- A61B 5/00 (2006.01)
- A61B 5/024 (2006.01)
- G06F 19/00 (2011.01)
- A61B 5/021 (2006.01)

(52) U.S. Cl.
CPC ............... *A61B 5/002* (2013.01); *A61B 5/021* (2013.01); *A61B 5/024* (2013.01); *A61B 5/02405* (2013.01); *A61B 5/411* (2013.01); *A61B 5/7275* (2013.01); *G06F 19/3418* (2013.01); *G06F 19/3456* (2013.01); *G06F 19/3475* (2013.01); *G06F 19/3481* (2013.01); *A61B 5/0022* (2013.01)

(58) Field of Classification Search
USPC ......... 600/300, 301; 340/573.1–576; 705/2–4
See application file for complete search history.

(56) References Cited

U.S. PATENT DOCUMENTS

| | | | | |
|---|---|---|---|---|
| 5,311,876 A * | 5/1994 | Olsen et al. | .................... | 600/544 |
| 5,564,429 A | 10/1996 | Bornn et al. | .................... | 128/696 |
| 5,752,913 A * | 5/1998 | Oka | .............................. | 600/300 |
| 5,772,585 A * | 6/1998 | Lavin et al. | .................... | 600/300 |
| 5,794,219 A | 8/1998 | Brown | ............................ | 705/37 |
| 5,832,448 A | 11/1998 | Brown | ............................ | 705/2 |
| 5,897,493 A | 4/1999 | Brown | .................... | 600/300 |
| 5,899,855 A | 5/1999 | Brown | .................... | 600/301 |
| 5,960,403 A | 9/1999 | Brown | | |
| 5,997,476 A | 12/1999 | Brown | .................... | 600/300 |
| 6,032,199 A | 2/2000 | Brownell | .................... | 705/2 |
| 6,039,688 A * | 3/2000 | Douglas et al. | .............. | 600/300 |
| 6,050,940 A | 4/2000 | Braun et al. | ................ | 600/300 |
| 6,082,776 A * | 7/2000 | Feinberg | .................... | 283/72 |
| 6,101,478 A | 8/2000 | Brown | ............................ | 705/2 |
| 6,139,494 A * | 10/2000 | Cairnes | .................... | 600/300 |
| 6,161,095 A | 12/2000 | Brown | ............................ | 705/2 |
| 6,167,362 A | 12/2000 | Brown et al. | .................... | 703/11 |
| 6,168,563 B1 | 1/2001 | Brown | .................... | 600/301 |
| 6,175,752 B1 * | 1/2001 | Say et al. | .................... | 600/345 |
| 6,246,992 B1 | 6/2001 | Brown | ............................ | 705/2 |
| 6,248,065 B1 | 6/2001 | Brown | .................... | 600/300 |
| 6,270,455 B1 | 8/2001 | Brown | .................... | 600/300 |
| 6,302,844 B1 * | 10/2001 | Walker et al. | .................. | 600/300 |
| 6,368,273 B1 | 4/2002 | Brown | .................... | 600/300 |
| 6,381,577 B1 | 4/2002 | Brown | ............................ | 705/2 |
| 6,398,740 B1 * | 6/2002 | Lavery et al. | .................. | 600/549 |

(Continued)

OTHER PUBLICATIONS

U.S. Appl. No. 10/956,681, filed Oct. 1, 2004, Kiff et al. Entitled : "Mobile Telephonic Device and Base Station".

(Continued)

*Primary Examiner* — William Thomson
*Assistant Examiner* — Bobby Soriano
(74) *Attorney, Agent, or Firm* — Husch Blackwell LLP

(57) ABSTRACT

A physiological condition monitor can provide substantially real-time feedback to an individual being monitored. The feedback can be in the form of graphical displays of real-time trends. Both audible and visual warnings can be provided to the individual in response to results of trend analysis.

14 Claims, 2 Drawing Sheets

(56) References Cited

U.S. PATENT DOCUMENTS

| | | | |
|---|---|---|---|
| 6,402,691 B1 | 6/2002 | Peddicord et al. | 600/300 |
| 6,524,239 B1 * | 2/2003 | Reed et al. | 600/300 |
| 6,579,231 B1 * | 6/2003 | Phipps | 600/300 |
| 6,612,984 B1 | 9/2003 | Kerr, II | 600/300 |
| 6,723,046 B2 | 4/2004 | Lichtenstein et al. | |
| 6,745,764 B2 * | 6/2004 | Hickle | 128/203.12 |
| 6,746,398 B2 * | 6/2004 | Hervy et al. | 600/300 |
| 7,039,628 B2 * | 5/2006 | Logan, Jr. | 1/1 |
| 7,225,029 B2 * | 5/2007 | Shankar et al. | 607/60 |
| 2002/0183599 A1 | 12/2002 | Castellanos | |
| 2003/0088439 A1 * | 5/2003 | Grushka | 705/2 |
| 2004/0093239 A1 | 5/2004 | Ott et al. | |
| 2005/0065815 A1 * | 3/2005 | Mazar et al. | 705/2 |
| 2005/0114179 A1 * | 5/2005 | Brackett et al. | 705/2 |
| 2005/0197860 A1 * | 9/2005 | Joffe et al. | 705/2 |
| 2005/0203349 A1 * | 9/2005 | Nanikashvili | 600/300 |
| 2005/0203773 A1 * | 9/2005 | Soto et al. | 705/2 |
| 2006/0004603 A1 * | 1/2006 | Peterka et al. | 705/2 |
| 2006/0071798 A1 | 4/2006 | Kiff | |

OTHER PUBLICATIONS

European Search Report, mailed Sep. 24, 2009 corresponding to European application No. EP 06 77 3919.

\* cited by examiner

TREND MONITORING SYSTEM WITH MULTIPLE ACCESS LEVELS

FIELD OF THE INVENTION

The invention pertains to systems that monitor one or more physiological characteristics of an individual. More particularly, the invention pertains to such systems which incorporate trend analysis.

BACKGROUND OF THE INVENTION

Known in-home monitoring systems monitor certain vital signs of residents or patients and transmit that information to a central computer at a remote location that can then be accessed by medical personnel and caregivers. At that site, trend information can be obtained and evaluated.

If a parameter is out of a normal range, then a medical monitor or caregiver can communicate that to the resident by electronic means, a virtual visit or an actual visit to the home. In order to keep costs low, it is advantageous to not have to make actual home visits unless necessary to correct the situation or provide medical attention.

In view of an aging population there is a continuing need to support those residents who are able to and want to continue to live in their present residences. It would thus be desirable and useful to make available to such residents health related trend information. Probably such trend information could be developed locally, at the residence, and presented to the resident with relatively short turnaround times.

DETAILED DESCRIPTION OF THE EMBODIMENTS

Figure 1:
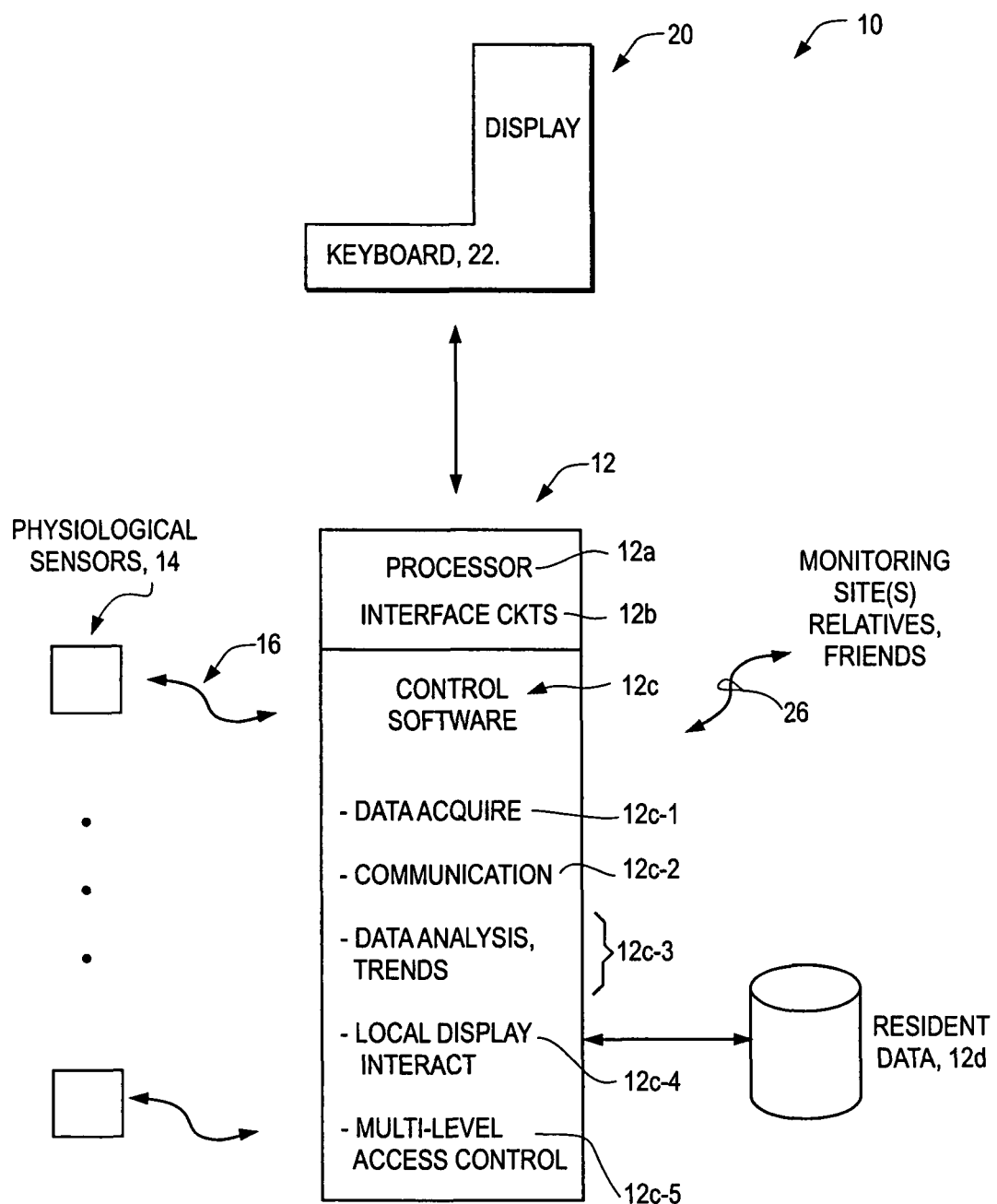
FIG. 1 is block diagram of a system in accordance with the invention.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

Disclosed embodiments of the invention provide data and trend analysis in a home or residence for the resident to view and use to adjust behavior accordingly. This provides a feeling of self-reliance and respect in being able to control their behavior without outside influence.

In one aspect of the invention normal physiological limits can be presented in a trend analysis. However, residents can observe where they are relative to the normal range. The normal limits for a given resident may be unique to that person and pre-established based upon historical data collected for that resident.

The advantage of having the plot and trend analysis of data representing an individual's physiological measurements presented with at least one limit is that person then can themselves recognize any trend that is starting to deviate from normal before it passes into an abnormal range for that person. This provides immediate feedback to the person to continue with their present behaviors or to adjust their behaviors. For example, a resident starting to see his/her glucose levels deviating from normal could relate it back to the their diet. They could realize they should alter their diet or recognize deviations from their diet that affect glucose.

In accordance with this invention, the resident can perform a physiological measurement at any time he/she wishes. That data can then be incorporated into the trend analysis. The trend analysis can also include provisions for resident inputs that may be of value in interpreting the physiological sensor readings. For example, taking a glucose reading before eating and after eating may produce different results. Such results can then be charted differently for the resident to observe the results of their behavior.

Taking a physiological reading before and after exercise can also produce different results. The resident can enter critical input information that is used in the trend analysis.

Further in accordance with this invention, the processing of sensor data can be adjusted for the conditions prior to or at the time of obtaining that data. These adjustments can be presented in the trends.

In one aspect of the invention, the sensor data can be input into the system. If any abnormalities are detected, the resident can be asked to report the conditions prior to the physiological reading to determine an acceptable reason for the abnormality, such that it may actually be normal for that measurement. For example, to simply take the blood pressure and enter it into the system is not adequate to determine the health status of the resident.

If the blood pressure is high, then it is important to know if some behavior contributed to that such as exercising in some form immediately before taking the sensor readings. Exercise and food/water consumption may alter some of the physiological measurements. The system can ask questions that may relate to when food and water were consumed or when and how much exercise was performed or the activity of the patient.

The taking of medications may alter the physiological measurements. Medications can be entered by the resident, possibly answering questions from the system.

A primary advantage of embodiments of this invention is that residents themselves can effectively determine what charts are presented by the inputs they enter into the system. If they input information that relates to their heart rate recovery after exercising, the systems can automatically generate a graph or a chart for them with that information.

The resident can enter information into the system for processing to determine the health status of the person. The system may instruct the resident to take some specific action such as resting or taking medications and then to schedule their physiological measurements again at a later time. The system may also reschedule the next time when the resident will measure his/her physiological data based upon the response of the resident in following a specific action. All data entered may still be used to evaluate the resident's health.

The trend information in the display can also involve multiple levels of concern. One level could be related to the resident evaluating their behaviors. A second level could relate to a pending critical condition that needs emergency response.

The system can send information to a remote location at different priorities based upon the trend information developed on-site. This is a more interactive exchange of information between the system and the resident to provide a more accurate assessment of the health and wellbeing of the resident.

An important aspect for any display of information relative to a resident is privacy and the access to that information by others. The resident may have certain access needs that are not appropriate for a visitor or neighbor or caregiver. A doctor may have more extensive needs for information concerning a resident in certain areas but not in others.

Embodiments of the invention can further provide multi-level access to medical information of a resident by use of different passwords.

An emergency responder could be unknown at the time passwords are predetermined and there should be no passwords related to sustaining the life of the resident. An emergency responder in a medical emergency may be presented with medications being taken, allergies, medications that are adverse to the patient (especially in connection with the medications being taken). The emergency responder may also be presented with graphical information related to trends of physiological measurements that may be relevant to the emergency situation. Seeing the trend information can be of critical value in determining temporary treatment and sustaining of life until arriving at the hospital.

In another embodiment, the system could automatically print a copy of information that would then be immediately available to the emergency responder. These printed copies may exclude resident name or identification information in case they get misplaced or lost. The resident could pre-approve what information can be released to the emergency responders so as to not violate his/her privacy.

In one aspect of the invention the information for emergency responders is only available without passwords in the presence of the resident. If a caregiver uses a remote access to the system during a medical emergency, then the caregiver would need to use a password which would then give him/her access to their normal information level plus the emergency response information level.

By way of example, for an access level 1 password, a caregiver may be presented with medications being taken and the trend graphs of important physiological measurements of the resident. Since the caregiver is not prescribing medications, their access would not include the same degree of information as the doctor or resident. If there is presently a critical emergency situation taking place while the caregiver is in attendance, the caregiver then becomes a part of the emergency response team.

For an access level 2 password, the requestor can be presented with the same information as the caregiver and emergency responder plus other medical information that is more private to the resident—if requested. That can include history of doctor visits and medical matters, related medical information, schedules, costs, insurance, etc.

For an access level 3 password, a doctor can access diagnosis and testing information which can include raw data as well as summaries and notes on discussions with other physicians. This could be a more complicated language intended for exchange of information between physicians. The physician would be issued a password that could then be stored in a special data bank or location accessed by the doctors or their representatives. They could change that password to one of their choosing.

If a cell phone access is available and the phone incorporates text and video, it is possible that the same passwords can provide the same levels of information. For example, if a doctor is out of the office when called for an emergency response, the doctor can call into the system and obtain the emergency or other information remotely. In the case of remote access, the doctor would need to use his/her password even as an emergency responder. Other access levels could be provided without departing from the spirit and scope of this invention.

FIG. 1. illustrates various aspects of a system 10 which embodies the present invention. System 10 incorporates a base or control unit 12 which can carry out many, if not all of the functions of a residential monitoring system.

Residential meeting systems have been disclosed for example in U.S. Pat. No. 6,402,691 B1 entitled In-Home Patient Monitoring System which issued Jun. 11, 2002. Another such system has been disclosed in pending U.S. patent application Ser. No. 10/956,681 filed Oct. 1, 2004 and entitled Mobile Telephonic Device and Base Station. The '681 application is assigned to the Assignee hereof and incorporated herein by reference.

Unit 12 includes a programmable processor 12a as well as interface circuitry 12b, which would be understood by those of skill in the art, for receiving information from members of a plurality 14 of physiological sensors. The members of the plurality 14 could include for example and without limitation blood pressure monitors, heart rate monitors, temperature monitors, respiration sensors and the like all without limitation.

The sensors of 14 communicate with the unit 12 by a wired or wireless medium indicated generally at 16. It will be understood that the nature and characteristics of the media of 16 are not limitations of the present invention.

Unit 12 incorporates control software 12c having a variety of different functional characteristics including data acquisition software 12c-1, communication software 12c-2, data and trend analysis software 12c-3, local display and interacting control software 12c-4 and multi-level access control software for 12c-5. In accordance with the above description and as described in more detail subsequently, signals received from members of the plurality of sensors 14 can be acquired and analyzed by software 12c for purposes of informing residents, substantially in real-time, if desired, as to ongoing trends.

Trend information can be presented on a display unit 20. A resident who might be viewing trend information on the display 20 can interact with unit 12 via a touch screen or alternately keyboard 22. It will be understood that the exact characteristics of the display 20 and input devices such as keyboard 22 are not limitations of the present invention.

Software 12c can also incorporate multi-level access control software 12c-5 which can make available to the resident, emergency personnel, caregivers, relatives or medical monitors various degrees of residential medical and personal data 12d. The data 12d can be stored over a period of time and can be used to establish baselines for the resident.

Figure 2:
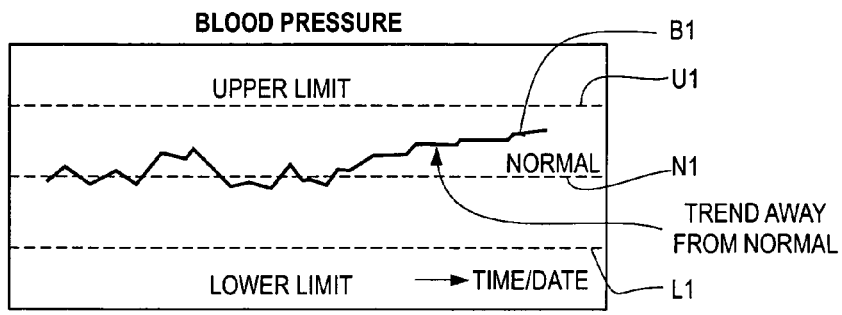
FIG. 2 is a graph illustrating blood pressure trend information.

FIG. 2 is a representative graph of blood pressure which might be sensed via one of the sensors 14, and, as a result of analysis carried out by software 12c-3 the trend information of FIG. 2 can be presented on display 20 for the resident. As illustrated in FIG. 2, upper and lower limits U1, L1 can be displayed as well as a nominal or normal value N1, which might be based on medical information and data 12d of the resident.

The sensed blood pressure information B1 as illustrated in FIG. 2 as trending away from the nominal or normal value N1 for the resident. Such a display provides immediate feedback to the resident that a potential trend of concern is developing.

The trend information can be forwarded via processor 12a, unit 12, and a medium 26, which could be wired or wireless, to one or more monitoring sites, sites maintained by relatives and/or friends for purposes of alerting such individuals as to developing trends of potential concern. It will be understood that the medium 26 could include one or more computer networks, such as the Internet.

Figure 3A:
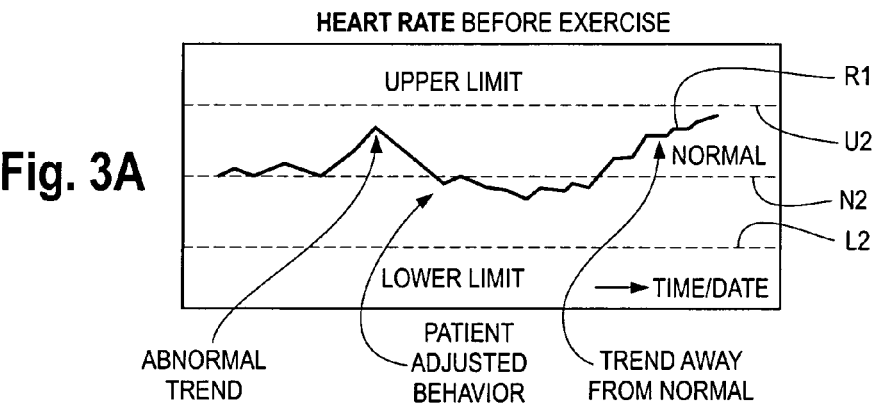
FIGS. 3A, 3B and 3C illustrate heart rate trend information under various conditions.
Figure 3B:
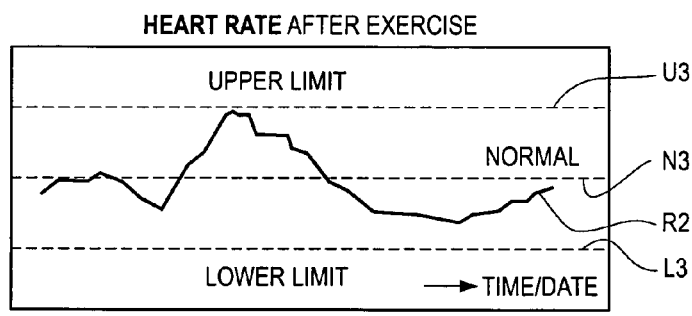
Figure 3C:
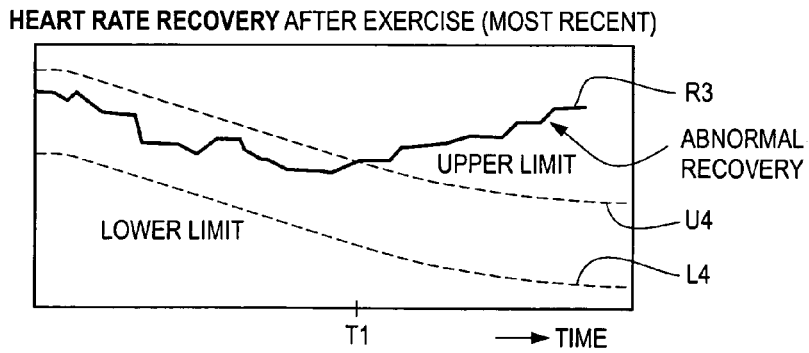

FIGS. 3A, 3B and 3C illustrate additional aspects of the interactive software 12c relative to data received from a heart rate sensor of the plurality 14. FIG. 3A illustrates ongoing heart rate prior to exercise taking place with upper limit U2, lower limit L2 and nominal normal N2. The illustrated R1 various above and below the nominal normal value N2 depending on in part behavior of the resident for example resting, moving around or the like prior to exercise.

FIG. 3B represents ongoing trend information relative to heart rate subsequent to exercise. As illustrated in FIG. 3B the post exercise rate R2 once again is presented in combination with the upper limit U3 lower limit L3 and a nominal or normal post exercise value N3. The heart rate data R2 illustrates an increase due to exercise and a subsequent decrease. Such information could be useful to the resident as well as to other individuals in communication with unit 12 to ascertain the benefits of one or more exercise programs.

FIG. 3C illustrates alternate trend information, namely, heart rate recovery after exercise as a function of time. Upper and lower limits U4, L4 bracket part of measured heart rate R3. While falling within normal limits subsequent to exercise the resident's heart rate R3 exceeds upper limit U4 at time T1 which could be indicative of an adverse developing condition.

Feedback can be provided to the resident automatically via unit 12 as well as from the remote monitoring sites via medium 26 to alert the resident to a need to modify behavior, take medication and/or the like. Additionally, the accumulated resident data 12d can be accessed by the multi-level control software 12c-5 both locally and remotely to further evaluate the resident's condition in the event of adverse trends as illustrated in FIG. 3C.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A system comprising:
    at least one in-home sensor of a physiological parameter of a person;
    control circuitry and executable software, local to the sensor, that provide data analysis and that develop trend information on-site in a home of the person, the control circuitry receives information from the at least one sensor via a wired or wireless medium, the software evaluates the information from the at least one sensor relative to at least one baseline;
    multi-level access control software, local to and coupled to the control circuitry, the multi-level access control software providing access to medical and personal information of the person at a predetermined level in response to a locally entered password, the predetermined level of accessible information selected from a plurality of stored levels of medical and personal information, said multi-level access control software having an access level for caregivers based upon entry of a first password by the caregiver and another access level for a physician based upon entry of a second password by the physician and wherein pre-approved portions of the medical and personal information of the person is automatically available to emergency responders without a password only in the presence of the person;
    an input device, local to and coupled to the control circuitry, the input device enabling the person to manually enter condition related information; and
    an output device, local to and coupled to the control circuitry, the control circuitry visually presenting substantially real-time trend information to the person based upon the information from the at least one sensor and the input device.

2. A system as in claim 1 which includes a plurality of sensors of physiological parameters of the person with members of the plurality local to the control circuitry.

3. A system as in claim 1 where the software evaluates the information relative to a second baseline, one baseline is displaced in amplitude relative to the other.

4. A system as in claim 3 where the output device includes a display device for visually presenting trend information, and software for providing a person specific graph on the display device substantially immediately in response to condition related inputs received from the person.

5. A system as in claim 4 where alarm indicia are produced indicative of the information falling outside of a region, bounded at least in part, by the baselines.

6. A system as in claim 5 where the alarm indicia include at least one of an audible or a visible indicator.

7. A system as in claim 5 which includes software that enables the person to enter condition related information.

8. A system as in claim 7 where the software evaluates any entered condition related information relative to the baselines.

9. A system as in claim 8 where the output device verbally emits trend related information.

10. A system as in claim 9 which includes communications software to transmit trend related indicia to a displaced location.

11. A monitoring system comprising:
    a plurality of in-home sensors of different physiological conditions of an individual;
    control circuits wired to communicate or wirelessly communicating at least some of the sensors and receiving indicia indicative of respective physiological conditions of the individual;
    a display unit local to the control circuits and coupled thereto, the display unit including a manually operable input device with the control circuits acquiring inputs entered by the individual using the control device with the control circuits including control software that provides data analysis and that develops trend information on-site in a home of the individual, the control software is responsive to the inputs from the plurality of in-home sensors and the manually operable input device and automatically generates condition indicating graphs on the display unit; and
    multi-level access control software, local to and coupled to the control circuits, the multi-level access control software providing access to medical and personal information of the individual at a predetermined level in response to a locally entered password, the predetermined level of accessible information selected from a plurality of stored levels of medical and personal information, said multi-level access control software having an access level for caregivers based upon entry of a first password by the caregiver and another access level for a physician based upon entry of a second password by the physician and wherein pre-approved portions of the medical and personal information of the individual is automatically available to emergency responders without a password only in the presence of the individual.

12. A system as in claim 11 where the control circuits execute local analysis software that generates the displayed condition indicating graphs.

13. A system as in claim 2 where at least one of the plurality of sensors is a sensor selected from a group consisting of a blood pressure monitor, a heart rate monitor, a temperature monitor, a respiration sensor, an electrocardiograph, an electroencephalograph, a pulse oximeter, and a blood glucose meter.

14. A system as in claim 11 where at least one of the plurality of sensors is a sensor selected from a group consisting of a blood pressure monitor, a heart rate monitor, a temperature monitor, a respiration sensor, an electrocardiograph, an electroencephalograph, a pulse oximeter, and a blood glucose meter.

* * * * *